United States Patent
van Bennekom et al.

(10) Patent No.: US 10,751,446 B2
(45) Date of Patent: Aug. 25, 2020

(54) USE OF A PRECIPITATION-HARDENING OR SOLID-SOLUTION-STRENGTHENING, BIOCOMPATIBLE COBALT-BASED ALLOY AND METHOD FOR PRODUCING IMPLANTS OR PROSTHESES BY MEANS OF MATERIAL-REMOVING MACHINING

(71) Applicant: Deutsche Edelstahlwerke Specialty Steel GmbH & Co. KG, Witten (DE)

(72) Inventors: André van Bennekom, Ainring (DE); Horst Hill, Grefrath (DE); Oliver Ripkens, Kerken (DE)

(73) Assignee: Deutsche Edelstahlwerke Specialty Steel GmbH & Co., Witten (DE)

( * ) Notice: Subject to any disclaimer, the term of this patent is extended or adjusted under 35 U.S.C. 154(b) by 81 days.

(21) Appl. No.: 16/070,337

(22) PCT Filed: Feb. 3, 2017

(86) PCT No.: PCT/EP2017/052356
§ 371 (c)(1),
(2) Date: Jul. 16, 2018

(87) PCT Pub. No.: WO2017/134209
PCT Pub. Date: Aug. 10, 2017

(65) Prior Publication Data
US 2019/0022275 A1    Jan. 24, 2019

(30) Foreign Application Priority Data

Feb. 3, 2016 (EP) .................................. 16154097

(51) Int. Cl.
| | | |
|---|---|---|
| *C22C 19/07* | (2006.01) | |
| *A61L 27/04* | (2006.01) | |
| *C22F 1/10* | (2006.01) | |
| *A61C 13/00* | (2006.01) | |
| *A61C 13/20* | (2006.01) | |

(52) U.S. Cl.
CPC ........ *A61L 27/045* (2013.01); *A61C 13/0022* (2013.01); *A61C 13/20* (2013.01); *C22C 19/07* (2013.01); *C22F 1/10* (2013.01); *A61L 2430/12* (2013.01)

(58) Field of Classification Search
CPC .......... C22F 1/10; C22C 19/07; A61L 27/045; A61C 13/0022; A61C 13/20
See application file for complete search history.

(56) References Cited

U.S. PATENT DOCUMENTS

| | | |
|---|---|---|
| 4,116,724 A | 9/1978 | Hirschfeld et al. |
| 4,788,034 A | 11/1988 | Brandis et al. |
| 7,520,947 B2 | 4/2009 | Kennedy et al. |
| 2006/0096672 A1 | 5/2006 | Burgermeister et al. |
| 2008/0241788 A1 | 10/2008 | Bauer et al. |

FOREIGN PATENT DOCUMENTS

| | | |
|---|---|---|
| DE | 4229599 C1 | 8/1993 |
| DE | 19704530 A1 | 8/1998 |
| EP | 0257262 A1 | 3/1988 |
| EP | 1657318 A1 | 5/2006 |
| EP | 1972321 A1 | 9/2008 |
| GB | 2270324 A | 3/1994 |
| JE | 2621789 A1 | 12/1977 |
| JP | 200946760 A | 3/2009 |
| JP | 2010502468 A | 1/2010 |
| JP | 2014074227 A | 4/2014 |
| WO | 2001013970 A1 | 3/2001 |
| WO | 2005007909 A2 | 1/2005 |
| WO | 2008033867 A2 | 3/2008 |

OTHER PUBLICATIONS

"Micromachining of Ceramic Surfaces: Hydroxyapatite and Zirconia," Journal of Materials Processing Technology, 2012, vol. 212, No. 3, pp. 614-624.
"3D printing of dental restorations", Metalpowder Report, 2013, pp. 32-33, No. 2.

*Primary Examiner* — Jessee R Roe
(74) *Attorney, Agent, or Firm* — The Webb Law Firm

(57) ABSTRACT

The invention shows possibilities which allow simplified production of implants or prostheses, specifically of dental implants or prostheses, by applying subtractive processes. For this purpose, the invention proposes the use of a precipitation-hardening or solid-solution-strengthening, biocompatible cobalt-based alloy for the production of blanks. Such blanks are provided in the soft state. Subsequently, each component (implant or prosthesis) is produced from the soft blank by means of material-removing machining. Subsequently, a heat-treatment of the implant or prosthesis then takes place to adjust the hardness thereof by means of precipitation hardening or solid-solution formation.

11 Claims, No Drawings

USE OF A PRECIPITATION-HARDENING OR SOLID-SOLUTION-STRENGTHENING, BIOCOMPATIBLE COBALT-BASED ALLOY AND METHOD FOR PRODUCING IMPLANTS OR PROSTHESES BY MEANS OF MATERIAL-REMOVING MACHINING

CROSS-REFERENCE TO RELATED APPLICATIONS

This application is the United States national phase of International Application No. PCT/EP2017/052356 filed Feb. 3, 2017, and claims priority to European Patent Application No. 16154097.6 filed Feb. 3, 2016, the disclosures of which are hereby incorporated in their entirety by reference.

BACKGROUND OF THE INVENTION

Field of the Invention

The invention relates to a use of a precipitation-hardening or solid-solution-strengthening, biocompatible cobalt-based alloy and to a method for producing implants by means of material-removing machining.

If the present document contains references to concentrations of alloys, said references always refer to the weight, unless explicitly stated otherwise.

For the production of components which are to be used in or on a human or animal body, a broad spectrum of materials is used. This extends from plastics materials through ceramic materials and precious metal materials to metal materials which consist of non-precious metals.

The description "component for use in or on a human or animal body" in this case includes implants which are permanently installed in the body, such as screws, splints, braces, parts of hip or knee joints, dental abutments or other dental implants which are permanently anchored in the jaw and other parts implanted as a replacement for natural bones or joints, as well as prostheses which are temporarily or permanently attached to the body, such as parts of dental prostheses (bridges, partial dentures or full dentures) or tools which are required in particular for dental treatment. Said materials based on non-precious metals include in particular Co-based or Ni-based alloys such as CoCr and NiCr materials, which are typically used for dental applications, but also for joint implants, in particular hip or knee implants.

Materials for implants or prostheses must be sufficiently corrosion-resistant and have optimised biocompatibility. Therefore, when in use, said materials must not have any harmful effects on the body in which or on which the components produced therefrom are used, and also must not trigger any other reactions which could have adverse effects on well-being or health.

At the same time, implant or prosthesis materials must have a mechanical property, such as strength, robustness and the like, which is sufficient for the intended use.

Lastly, such materials must also be easy to handle and process in order to be able to achieve the design of implants or prostheses which, in many instances, is particularly delicate and individually adapted in each case.

Description of Related Art

In the case of cobalt-based materials of the type mentioned here, three manufacturing routes are established in the field of dental technology, which each have different requirements in terms of material behaviour.

These include conventional casting processes in which each implant or each prosthesis is formed on the basis of a model. In the example of an implant being used in the oral cavity, for this purpose, firstly a negative mould of the oral cavity is produced by means of a casting compound. Based on this, a lost mould is produced, in which the molten metal is cast. Subsequently, this is generally followed by mechanical secondary machining to ensure an optimal adaptation of the shape of the implant. If the implant or prosthesis is a denture, then after the implantation or arrangement in the oral cavity, visible parts are conventionally provided with a ceramic veneer. In this case, the metal material of the implant or the implant must have not only optimised mechanical properties and equally optimised compatibility, but also optimised suitability for the application of the ceramic veneer thereto, which is generally carried out by means of baking. Prostheses which are used as dentures and are continually kept in the oral cavity are conventionally attached to an abutment implanted in the jaw or to an existing tooth.

As an alternative to the conventional casting processes, what are known as additive manufacturing processes are known for producing implants. These are generally based on metal powders and are also used in particular in the production of prostheses or implants which are used in the oral cavity. Additive processes generally include 3D printing and specifically laser sintering or laser melting. In the additive processes, a digital image of the oral cavity is generally created, and this image is used to generate a 3D model of the implant to be produced. In laser sintering, an alloy powder is then applied in layers according to the 3D model and sintered or melted by means of a laser beam. The advantage of additive processes of this type consists in the fact that complexly shaped implants can be achieved without having to consider the problems relating to demoulding that exist in conventional casting processes, and at the same time, it is possible to produce individually formed implant components on an industrial scale. The prior art relating to the 3D printing of dentures is summarised in the article "3D printing of dental restorations", metalpowder report, no. 2, March/April 2013, pages 32-33, whereas an example of a method for producing dental implants by means of laser sintering is described in EP 1 972 321 B1.

As a third method established in the prior art for producing in particular implants or prostheses that are used in dentistry, what are known as subtractive or removing processes should be mentioned. In these processes, a blank consisting of the respective implant material is provided, from which the respective implant is subsequently carved by means of cutting machining. For these processes as well, a digital image of the oral cavity or of the region in which the implant is to be used is firstly generated, and said image is used to generate a 3D model of the implant. Subsequently, the implant is generally produced from a solid block by milling the blank. Depending on the geometry of the implant to be produced, discs, cubes, cylinders or cuboids are used as blanks.

In order to be approved for use as an implant material, these materials must undergo extensive tests in which in particular the biocompatibility and durability thereof have to be proven. Due to the costs associated with these tests, there is a fundamental effort to use the same materials for the three established manufacturing routes. Accordingly, a broad range of properties are required of the implant materials.

One characteristic of conventional CoCr and NiCr materials which are provided for application specifically in the oral cavity is that they are naturally hard. This means that to adjust the final hardness and other mechanical properties thereof, no special heat treatment is required, but rather the required characteristics profile is present immediately after producing the respective alloy. For the manufacturing routes I (conventional casting process) and II (additive process), this does not present a problem, but rather is even generally desirable, since after the moulding production, each implant component is at the most be subjected to fine machining, such as grinding or polishing, and it is thus advantageous if the desired properties are already present in the material.

Conventional cobalt-based alloys for implants, depending on the composition thereof in the naturally hard state, achieve high strengths (yield strength >500 MPa), as a result of which a hardness of up to 40 HRC is produced.

These properties, which are advantageous per se for the intended purpose mentioned here, are an obstacle to removing material in the subtractive machining processes. In the cutting machining of the blank, the high hardness leads to increased tool wear and causes the machining to take longer.

In view of the prior art explained above, the problem is addressed of showing possibilities which allow simplified production of implants or prostheses, specifically of dental implants or prostheses, by applying subtractive processes.

SUMMARY OF THE INVENTION

The invention accordingly proposes the use of a precipitation-hardening or solid-solution-strengthening, biocompatible cobalt-based alloy for the production of blanks which are provided so that, in the soft state thereof, implants or prostheses are carved out of said blanks by means of cutting machining, which implants or prostheses are subjected to a heat treatment after the cutting machining in order to adjust the final hardness of the implants or prostheses by means of precipitation hardening or solid-solution formation.

The invention also proposes, to produce an implant, carrying out at least the following work steps:
  providing a soft blank, which consists of a precipitation-hardening or solid-solution-strengthening, biocompatible cobalt-based alloy,
  carving an implant or the prosthesis out of the soft blank by means of cutting machining,
  heat-treating the implant or the prosthesis to adjust the hardness by means of precipitation hardening or solid-solution formation.

What the use according to the invention and the method according to the invention have in common is thus that each blank from which each implant or prosthesis component is to be manufactured is produced from a precipitation-hardening or solid-solution-strengthening Co-based material, which, in the initial state thereof, i.e. the state in which it is provided for the material-removing machining, has not yet achieved the final hardness thereof, but rather is designed in such a way that said material reaches the final hardness thereof only after a final heat treatment as a result of the precipitations forming in the structure of the material.

DESCRIPTION OF THE INVENTION

The soft structure of the blank provided according to the invention, which is characterised by low hardness, can be adjusted in particular by subjecting the blank to solution-annealing before the material-removing machining, in which solution-annealing process the hardness of said blank is reduced by triggering the break-up of intermetallic phases and grain growth.

The production of the blank can be carried out in a conventional manner by casting or by applying powder-metallurgy processes which are likewise known per se. Examples include casting, casting and shaping, precision casting, powder and hot isostatic pressing.

Due to the low hardness of the blank provided according to the invention by comparison with the final hardness of each component, said blank can be machined with low tool wear and at a greater speed. Material is typically removed by means of cutting processes, in particular by means of milling. However, all other processes which allow effective removal of material whilst utilising the low hardness present in a blank provided according to the invention are also suitable for this purpose.

The mechanical properties required from the finished implant or prosthesis component are adjusted according to the invention by a heat treatment which is carried out after the material-removing, shaping machining. This heat treatment brings about the precipitation hardening or solid-solution formation and, as a consequence thereof, adjusts the high strengths that the implants should have in particular for the dental sector. Precipitation hardening and solid-solution formation can of course occur in combination and jointly contribute to increasing hardness. By adjusting the respective alloys, the effect of precipitation hardening can exceed that of solid-solution formation and vice versa.

Typically, the blanks provided according to the invention are discs from which each implant is carved by means of milling. Such discs are also referred to in technical terminology as "milling discs".

In this case, the invention is particularly suitable for producing dental implants which are introduced as fixing means for dentures or directly as dentures or as aids for fixing dentures in the jaw, or for dental prostheses which are attached to the jaw as or for a denture.

Co-based alloys, of the type provided by the invention for use as a material for blanks from which implants or prostheses, in particular dental implants or prostheses, are produced by removing material, are known per se from the prior art (e.g. EP 1 972 321 B1). However, in said document, said alloys are used for other uses or other production processes.

Only the invention has recognised that these alloys, which are known per se, can be combined or heat treated in such a way that, as a blank, they have optimised properties for material-removing machining and, by means of a final heat treatment following the material-removing machining, can be brought into line with the mechanical properties required by the respective implant or prostheses components.

An alloy specification which is suitable for the purpose according to the invention accordingly provides that the cobalt-based alloy consists of (in % by weight)
  C: up to 0.5%
  Si: up to 2.5%
  Cr: 22-29%,
  Mn: up to 1%,
  Ni: up to 3%,
  Fe: up to 3%,
  Ce: up to 1%,
  Ga: up to 5%,
  B: up to 2.5%
and in each case at least one of the elements forming hardening precipitations or solid solutions from the group comprising "Mo, W, Nb, Al, Ti", in which, for the concentrations of these elements, where present, the following proportion applies
  Mo: 3-9%,
  W: 3-9%, Nb: 3-9%, Al: 0.1-6%, Ti: 0.1-6%, and as residue, Co and unavoidable impurities resulting from production.

Carbon can be present in the cobalt-based alloy used according to the invention in concentrations of up to 0.5% by weight. Carbon is generally an undesirable impurity since, as a result of precipitation of Cr-rich carbides, corrosion resistance is reduced. Optimally, therefore, the C concentration is limited to up to 0.1% by weight, in particular to less than 0.1% by weight.

Silicon can be present in the cobalt-based alloy used according to the invention in concentrations of up to 2.5% by weight. By adding silicon, the melting point and the viscosity of the molten mass are reduced. At the same time, silicon has the positive effect that the adhesion of a ceramic veneer which is optionally attached to the implant is improved by forming oxides or oxide compounds. To make use of this effect, the Si concentration of the Co alloy can be at least 0.8% by weight. Above 2% by weight, Si has no more property-improving effects.

In the cobalt-based alloy used according to the invention, chromium can be present in concentrations of from 22-29% by weight, in particular more than 22.00% by weight to less than 29.00% by weight. Chromium is required for corrosion resistance and is also involved in the solid-solution strengthening which is used according to the invention for the final adjustment of the hardness of each implant. Cr provides an optimal effect in the Co alloy used according to the invention when the Cr concentration is at least 23% by weight, in particular more than 23% by weight. At the same time, it has been shown that Cr concentrations of at most 27% by weight, in particular less than 27.00% by weight, ensure sufficient corrosion resistance specifically for regular use in the oral cavity.

Manganese in concentrations of up to 1% by weight, similarly to silicon, influences the viscosity of the molten mass and the adhesion to the veneer. In addition, sulphur is set by forming Mn sulphides. The positive effect of Mn in the Co alloy according to the invention can be used in particular when the Mn concentration is at least 0.01% by weight. Above 1% by weight, Mn has no more property-improving effects, the presence of Mn having an optimised effect when the Mn concentration is at most 0.5% by weight.

The nickel concentration in Co alloys used according to the invention is at most 3% by weight, but for use in particular in the oral cavity can be limited to concentrations of up to 0.1% by weight, in particular less than 0.1% by weight, in order to safely avoid allergic reactions. However, Co-based alloys having higher Ni concentrations can be suitable for knee or hip implants in order to achieve the mechanical properties of the material which are required for this intended use.

Iron ends up in the Co alloy used according to the invention as a result of the production process but is to be limited to at most 3% by weight, in particular less than 3.0% by weight, so as not to impair the corrosion resistance of the material. Negative effects of the present of Fe can be avoided particularly safely when the Fe concentration is limited to at most 0.5% by weight, in particular less than 0.1% by weight.

Cerium can be added to the alloy used according to the invention in concentrations of up to 1% by weight, since it greatly improves the bonding to the ceramic veneer by means of oxide formation.

Gallium can be present in the cobalt-based alloy used according to the invention in concentrations of up to 5% by weight. Gallium is also involved in the solid-solution strengthening and contributes to reducing the coefficient of thermal expansion.

In concentrations of up to 2.5% by weight, boron has comparable effects to Si. In addition, boron influences the oxide colour and, by forming boride precipitations, brings about an increase in hardness and strength. Concentrations above 2.5% by weight should be avoided, since otherwise the material would become very brittle.

In order to bring about the precipitation formation used according to the invention to adjust the hardness of the implant obtained after carrying out a subtractive process, the Co-based alloy used according to the invention contains at least one precipitation-forming element from the group comprising "Mo, W, Nb, Al, Ti", said elements being able to be present not only in isolation, but of course also in combination with one another in the Co alloy. For example, in each case two or more elements from the group of precipitation-forming elements provided according to the invention can be contained in the Co alloy.

Molybdenum in concentrations of from 3-9% by weight firstly increases corrosion resistance, but also brings about pronounced solid-solution strengthening and, as a consequence thereof, an effective increase in the hardness and strength of the Co alloy. At the same time, Mo contributes to reducing the coefficient of thermal expansion. The positive influence of Mo can be used particularly safely when the Mo concentration is at least 4% by weight. Practical trials have proven that, to use the positive influence of Mo, it is generally sufficient for the Mo concentration to be limited to at most 6% by weight.

In the Co alloy used according to the invention, tungsten in concentrations of from 3-9% by weight has a similar effect to molybdenum and thus firstly increases corrosion resistance, but also brings about pronounced solid-solution strengthening and, as a consequence thereof, an effective increase in the hardness and strength of the Co alloy. At the same time, W contributes to reducing the coefficient of thermal expansion. The positive influence of W can be used particularly safely when the W concentration is at least 4% by weight. Practical trials have proven that, to use the positive influence of W, it is generally sufficient for the W concentration to also be limited to at most 6% by weight.

Niobium can also be present in the Co alloy used according to the invention in concentrations of from 3-9% by weight. Niobium firstly leads to increased formation of Nb carbides provided that carbon is present. Unavoidable carbon impurities are thus set, with the consequence that the production of Cr and/or Mo carbides, which would reduce corrosion resistance, is prevented. The presence of Nb in the concentrations given thus indirectly leads to an increase in corrosion resistance. In other respects, the effect of Nb corresponds to that of tungsten or molybdenum. The positive influence of Nb can be used particularly safely when the Nb concentration is at least 4% by weight. Practical trials have proven that, to use the positive influence of Nb, it is generally sufficient for the Nb concentration to also be limited to at most 6% by weight.

Aluminium and titanium are equally involved in the formation of intermetallic phases and thus support precipitation hardening. With respect to the atomic percent thereof, they are interchangeable at a ratio of 1:1, where necessary. If present, the Al concentration of the Co alloy used according to the invention is 0.1-6% by weight, and the Ti concentration is 0.1-6% by weight, in particular up to 5% by weight, Al concentrations of at least 2% by weight or Ti concentrations of at least 1% by weight having proven to be particularly effective. At the same time, it has been shown that Al concentrations of a maximum of 4% by weight or Ti concentrations of a maximum of 3% by weight are regularly sufficient for the purposes according to the invention.

If necessary, before the cutting machining, the blank used and provided in each case according to the invention can be subjected to a heat treatment in which said blank is solution-annealed for a duration of from 15-600 min at a temperature of from 1050-1300° C. Optimal solution-annealing results are achieved when the solution period is at least 60 min, a maximum duration of the solution-annealing of at most 480 min having also been proven with respect to optimising the annealing result. It also contributes to optimising the result of the solution-annealing when the solution-annealing temperature is at least 1150° C., solution-annealing temperatures of a maximum of 1250° C. having also proven themselves in terms of optimisation. The solution-annealing brings about a reduction in hardness by triggering the break-up of intermetallic phases and grain growth so that the blanks have a hardness which is optimal for the material-removing machining.

The heating rate of the solution-annealing treatment should be at least 5 K/min and at most 20 K/min and thus be in the range typical for conventional solution-annealing furnaces. By means of the heating taking place in such a way, sufficient through-heating is ensured. Moreover, the heating rate has no effect on the resulting properties of the products produced according to the invention. After the solution-annealing, the blanks can be cooled to room temperature at a cooling rate of from 5-1000 K/min. When the cooling rate is slower, precipitations and recrystallisation are possible. The consequence would be an increase in hardness, which is undesirable in this work step. When cooling takes place considerably more fastly, warpage and even cracks could occur as a result of the thermal stresses. In this case, the cooling rates are to be selected within the limitations of the invention according to the cross section, and more specifically in each case so that the required cooling is achieved even in the core region.

The solution-annealing can be carried out conventionally under normal atmospheric conditions. In an equally conventional manner, the quenching after the solution-annealing can take place with air or water.

However, should the costs for the removal of the scale produced during the conventional solution-annealing under normal atmospheric conditions be avoided, then the solution-annealing treatment can be carried out under vacuum. The solution-annealing under vacuum prevents the oxidation and scaling of the respective blanks so that otherwise necessary secondary machining processes for removing scale or oxides can be minimised, and measurements required for the secondary machining can be avoided. The quenching can then be carried out by means of pressurised nitrogen in order to thereby also avoid oxidation and scale formation.

The optimal hardness for the material-removing machining is typically in the range of up to 35 HRC, in particular up to 28 HRC.

The hardness in HRC is conventionally determined in accordance with the processes defined in DIN EN ISO 6508-1.

To adjust the hardness thereof, the implants obtained by means of material-removing machining of the blanks can be kept at an ageing temperature of from 600-1000° C., in particular of up to 950° C., for an ageing duration of at least 5 min, in particular at least 60 min, and at most 600 min. Ageing temperatures of at least 700° C., above which the precipitation processes used according to the invention ensue particularly safely, have especially proven themselves in this case. In particular, for this purpose, the ageing temperature can be set to at least 750° C.

In this case, it has been shown that an ageing duration of from 5-150 min, in particular 5-120 min, is generally sufficient to bring about the precipitation processes used according to the invention. Depending on the respective alloy variants, good increases in hardness can already be achieved in the case of ageing durations of at most 20 min; in other alloy variants, ageing durations of at least 80 mins have proven to be advantageous in this respect. The heating rate should again be at least 5 K/min and at most 20 K/min in this case in order to reliably achieve proper through-heating using conventional furnaces. After the ageing, the blanks can be cooled to room temperature at a cooling rate of from 5-20 K/min.

In applications in the field of dental technology, no additional measures are generally required to achieve the hardness and strength levels sought for each use. In other cases, for example for the production of fastening components to be installed in or on the body, such as splints, screws, braces and the like, it can be expedient, however, to subject each product to work-hardening by means of cold deformation in order to increase the hardness and strength levels. Generally, the work-hardening takes place before the ageing, since then the blanks or the products formed therefrom are still soft and thus offer maximum hardening potential. Deformation processes which are carried out at temperatures of less than 200° C. are offered as an option for cold deformation for the work-hardening. These include processes in which deformations are produced by tension, compression or bending. These processes include swaging, drawing, straightening, stretching and the like. Typical degrees of deformation are up to 80% in this case. In this way, increases in hardness of up to 300% are possible (for example from 20 HRC in the initial state to 60 HRC in the cold-work-hardened state).

In the case where the implant is to be provided with a ceramic veneer, the temperature of the ageing can be selected in such a way that the ageing temperature corresponds to the baking temperature of the respective ceramic layers. Then the process of the precipitation hardening or solid-solution strengthening and the baking of the ceramic veneer can be combined with one another so that no additional process step is required, and the baking of the veneer has no additional effect on the precipitation hardening or solid-solution strengthening and the properties of the implant that are adjusted thereby.

This is possible by means of a specially adjusted combination of the chemical composition, the temperature and the duration of the heat treatment. However, the veneering can also be carried out retrospectively. The alloy according to the invention makes it possible in this case to coordinate the heat treatment and the process parameters of the veneering by means of a wide range of possible variations. The optimal functional properties can thus be adjusted without complicating the processing.

In order to demonstrate the feasibility of the invention disclosure, eleven different alloy systems "Variant I"-"Variant XI" were produced by means of casting. Starting from a Co—Cr—Si "base alloy", the alloy elements Mo, W, Nb, Al and Ti were varied.

In Tables 1-11, for each of the Variants 1-XI, a general alloy specification, the alloy specification which is considered to be optimal in the context of the general alloy specification, the analysis of the specifically examined sample, and a soft and a hard version of the alloy specification are indicated. The softer and harder versions are adjusted primarily by varying the concentrations of the alloy elements Al and Ti, since the effect of said alloy elements on the precipitation hardening is the most pronounced.

By contrast, varying Mo, W and Nb has an effect primarily on the solid-solution strengthening, as a result of which, the solution-annealing hardness changes. Mo, W and Nb, especially in combination with Al or Ti, bring about pronounced precipitation hardening. Without Al or Ti, precipitation hardening is still possible, but not as pronounced.

Except for the concentrations of Ti and Al, the concentrations of the respective alloy components of the samples specifically examined in each case were determined in a manner known per se using a spark spectrometer. The concentrations of Al and Ti were determined in each case in a manner likewise known per se using wet chemistry.

All samples were firstly solution-annealed at 1250° C. for eight hours in a vacuum. The heating took place at a heating rate of approx. 10 K/min. The quenching following the solution-annealing was carried out using nitrogen at 3.5 bar, which corresponded to a cooling rate of from 30-50 K/min in the trials carried out here.

In practice, after the solution-annealing, the material-removing machining of the blank would follow for the production of the implant.

The subsequent ageing tests were carried out in the temperature range of from 500-1000° C. (in steps of 100° C.) for ten hours in each case. The heating and cooling rates were approx. 10 K/min in each case. After each heat treatment, the hardness was measured in HRC. In Tables 1-11, for the specifically examined analyses, the average values from at least five individual measurements are indicated. In this case, Variant V does not correspond to the invention, since said variant does not contain any of the elements from the group provided according to the invention which bring about precipitation hardening or solid-solution strengthening.

The results shown in Tables 1-11 demonstrate that in particular the alloys containing Al and Ti tend towards pronounced precipitation hardening when the ageing is carried out in the temperature range of approximately 800° C.

Although Variants III and V show only a relatively low increase in hardness after the ageing treatment, said variants are suitable in particular for increasing hardness by means of work-hardening. In this way, it was possible to show that in Variants III and V, an increase in hardness of up to 60 HRC can be achieved by means of work-hardening of the samples.

Based on the samples from Variants VII-XI which were specifically examined, additional ageing tests were carried out in order to investigate the increase in hardness according to the ageing time. The ageing time was varied in steps of 20 min up to a total of 120 minutes. The tests also started from the state which was reached after the solution-annealing at 1250° C. which has already been explained. The rest of the parameters of the heat treatment were also not changed.

The results of the ageing tests are shown in Table 12. It should be noted that ageing times of more than 60 minutes already bring about a considerable increase in hardness. In Variants VII-X, after ageing for 120 minutes at 800° C., the hardness is already the same as after ageing for 10 hours.

The invention thus shows possibilities which allow simplified production of implants or prostheses, specifically of dental implants or prostheses, by applying subtractive processes. For this purpose, the invention proposes the use of a precipitation-hardening or solid-solution-strengthening, biocompatible cobalt-based alloy for the production of blanks. Such blanks are provided in the soft state in the course of the method according to the invention. Subsequently, each component (implant or prosthesis) is produced from the soft blank by means of material-removing machining. Subsequently, a heat-treatment of the implant or prosthesis then takes place to adjust the hardness thereof by means of precipitation hardening or solid-solution formation.

TABLE 1

| VARIANT I | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | 3.0-9.0 | 3.0-9.0 | — | — | — | <1.0 | <3.0 | <3.0 |
| Optimal *) | <0.1 | 0.8-2.0 | 23-27 | 4.0-6.0 | 4.0-6.0 | — | — | — | <0.5 | <0.1 | <0.5 |
| Soft variant *) | <0.1 | 0.8-2.0 | 23-27 | 3.0-5.0 | 3.0-5.0 | — | — | — | <0.5 | <0.1 | <0.5 |
| Hard variant *) | <0.1 | 0.8-2.0 | 23-27 | 5.0-7.0 | 5.0-7.0 | — | — | — | <0.5 | <0.1 | <0.5 |
| Examined example *) | 0.032 | 0.99 | 24.61 | 5.08 | 4.98 | — | — | — | <0.01 | <0.01 | 0.06 |

| Solution-annealing | Duration | Temperature | Hardness in HRC after solution-annealing |
|---|---|---|---|
|  | 8 | 1250 | 18.3 ± 2.0 |

| Ageing | Duration | Temperature | Hardness in HRC after ageing |
|---|---|---|---|
| Trial 1 | 10 h | 500° C. | 19.5 ± 2.7 |
| Trial 2 | 10 h | 600° C. | 19.4 ± 2.6 |
| Trial 3 | 10 h | 700° C. | 22.7 ± 2.2 |
| Trial 4 | 10 h | 800° C. | 31.2 ± 3.1 |
| Trial 5 | 10 h | 900° C. | 28.5 ± 1.8 |
| Trial 6 | 10 h | 1000° C. | 21.8 ± 1.0 |

*) Information in % by weight, residue Co and unavoidable impurities

TABLE 2

| VARIANT II | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | 3.0-9.0 | — | — | — | — | <1.0 | <3.0 | <3.0 |
| Optimal *) | <0.1 | 0.8-2.0 | 23-27 | 4.0-6.0 | — | — | — | — | <0.5 | <0.1 | <0.5 |
| Soft variant *) | <0.1 | 0.8-2.0 | 23-27 | 3.0-5.0 | — | — | — | — | <0.5 | <0.1 | <0.5 |

TABLE 2-continued

| | | | | | | | | | | | |
|---|---|---|---|---|---|---|---|---|---|---|---|
| Hard variant *) | <0.1 | 0.8-2.0 | 23-27 | 5.0-7.0 | — | — | — | — | <0.5 | <0.1 | <0.5 |
| Examined example *) | 0.005 | 1.01 | 24.01 | 5.02 | — | — | — | — | <0.01 | <0.01 | 0.06 |

| Solution-annealing | Duration | Temperature | Hardness in HRC after solution-annealing |
|---|---|---|---|
| | 8 | 1250 | 21.9 ± 2.3 |

| Ageing | Duration | Temperature | Hardness in HRC after ageing |
|---|---|---|---|
| Trial 1 | 10 h | 500° C. | 24.3 ± 1.5 |
| Trial 2 | 10 h | 600° C. | 25.3 ± 1.5 |
| Trial 3 | 10 h | 700° C. | 22.6 ± 1.8 |
| Trial 4 | 10 h | 800° C. | 22.7 ± 1.6 |
| Trial 5 | 10 h | 900° C. | 25.8 ± 1.8 |
| Trial 6 | 10 h | 1000° C. | 21.3 ± 1.7 |

*) Information in % by weight, residue Co and unavoidable impurities

TABLE 3

| VARIANT III | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | 3.0-9.0 | — | — | — | <1.0 | <3.0 | <3.0 |
| Optimal *) | <0.1 | 0.8-2.0 | 23-27 | — | 4.0-6.0 | — | — | — | <0.5 | <0.1 | <0.5 |
| Soft variant *) | <0.1 | 0.8-2.0 | 23-27 | — | 3.0-5.0 | — | — | — | <0.5 | <0.1 | <0.5 |
| Hard variant *) | <0.1 | 0.8-2.0 | 23-27 | — | 5.0-7.0 | — | — | — | <0.5 | <0.1 | <0.5 |
| Examined example *) | 0.011 | 0.96 | 24.89 | — | 5.16 | — | — | — | <0.01 | <0.02 | 0.06 |

| Solution-annealing | Duration | Temperature | Hardness in HRC after solution-annealing |
|---|---|---|---|
| | 8 | 1250 | 22.1 ± 2.1 |

| Ageing | Duration | Temperature | Hardness in HRC after ageing |
|---|---|---|---|
| Trial 1 | 10 h | 500° C. | 22.8 ± 0.5 |
| Trial 2 | 10 h | 600° C. | 23.3 ± 2.5 |
| Trial 3 | 10 h | 700° C. | 23.3 ± 3.2 |
| Trial 4 | 10 h | 800° C. | 20.7 ± 2.7 |
| Trial 5 | 10 h | 900° C. | 21.7 ± 1.7 |
| Trial 6 | 10 h | 1000° C. | 22.9 ± 3.1 |

*) Information in % by weight, residue Co and unavoidable impurities

TABLE 4

| VARIANT IV | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | — | 3.0-9.0 | — | — | <1.0 | <3.0 | <3.0 |
| Optimal *) | <0.1 | 0.8-2.0 | 23-27 | — | — | 4.0-6.0 | — | — | <0.5 | <0.1 | <0.5 |
| Soft variant *) | <0.1 | 0.8-2.0 | 23-27 | — | — | 3.0-5.0 | — | — | <0.5 | <0.1 | <0.5 |
| Hard variant *) | <0.1 | 0.8-2.0 | 23-27 | — | — | 5.0-7.0 | — | — | <0.5 | <0.1 | <0.5 |
| Examined example *) | 0.005 | 1.02 | 25.27 | — | — | 5.46 | — | — | <0.01 | <0.02 | 0.07 |

| Solution-annealing | Duration | Temperature | Hardness in HRC after solution-annealing |
|---|---|---|---|
| | 8 | 1250 | 32.1 ± 0.9 |

| Ageing | Duration | Temperature | Hardness in HRC after ageing |
|---|---|---|---|
| Trial 1 | 10 h | 500° C. | 30.0 ± 1.1 |
| Trial 2 | 10 h | 600° C. | 30.3 ± 1.3 |
| Trial 3 | 10 h | 700° C. | 43.3 ± 1.5 |
| Trial 4 | 10 h | 800° C. | 46.0 ± 1.0 |
| Trial 5 | 10 h | 900° C. | 42.1 ± 1.8 |
| Trial 6 | 10 h | 1000° C. | 36.1 ± 1.6 |

*) Information in % by weight, residue Co and unavoidable impurities;

TABLE 5

| VARIANT V not according to the invention | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | — | — | — | — | <1.0 | <3.0 | <3.0 |
| Optimal *) | <0.1 | 0.8-2.0 | 23-27 | — | — | — | — | — | <0.5 | <0.1 | <0.5 |

TABLE 5-continued

| | | | | | | | | | | | |
|---|---|---|---|---|---|---|---|---|---|---|---|
| Soft variant *) | <0.1 | 0.8-2.0 | 23-27 | — | — | — | — | — | <0.5 | <0.1 | <0.5 |
| Hard variant *) | <0.1 | 0.8-2.0 | 23-27 | — | — | — | — | — | <0.5 | <0.1 | <0.5 |
| Examined example *) | 0.011 | 0.96 | 24.89 | — | — | — | — | — | <0.01 | <0.02 | 0.07 |

| Solution-annealing | Duration | Temperature | Hardness in HRC after solution-annealing |
|---|---|---|---|
| | 8 | 1250 | 18.6 ± 1.7 |

| Ageing | Duration | Temperature | Hardness in HRC after ageing |
|---|---|---|---|
| Trial 1 | 10 h | 500° C. | 21.5 ± 1.7 |
| Trial 2 | 10 h | 600° C. | 20.6 ± 2.7 |
| Trial 3 | 10 h | 700° C. | 20.0 ± 1.4 |
| Trial 4 | 10 h | 800° C. | 19.8 ± 1.7 |
| Trial 5 | 10 h | 900° C. | 22.7 ± 2.3 |
| Trial 6 | 10 h | 1000° C. | 22.5 ± 2.4 |

*) Information in % by weight, residue Co and unavoidable impurities

TABLE 6

| VARIANT VI | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | — | | 0.1-6.0 | — | <1.0 | <3.0 | <3.0 |
| Optimal *) | <0.1 | 0.8-2.0 | 23-27 | — | — | | 2.0-4.0 | — | <0.5 | <0.1 | <0.5 |
| Soft variant *) | <0.1 | 0.8-2.0 | 23-27 | — | — | | 0.1-3.0 | — | <0.5 | <0.1 | <0.5 |
| Hard variant *) | <0.1 | 0.8-2.0 | 23-27 | — | — | | 3.0-6.0 | — | <0.5 | <0.1 | <0.5 |
| Examined example *) | 0.005 | 1.02 | 25.27 | — | — | | 3.58 | — | <0.01 | <0.02 | 0.07 |

| Solution-annealing | Duration | Temperature | Hardness in HRC after solution-annealing |
|---|---|---|---|
| | 8 | 1250 | 19.3 ± 2.0 |

| Ageing | Duration | Temperature | Hardness in HRC after ageing |
|---|---|---|---|
| Trial 1 | 10 h | 500° C. | 19.0 ± 1.4 |
| Trial 2 | 10 h | 600° C. | 19.0 ± 1.8 |
| Trial 3 | 10 h | 700° C. | 20.7 ± 2.2 |
| Trial 4 | 10 h | 800° C. | 25.1 ± 2.6 |
| Trial 5 | 10 h | 900° C. | 30.1 ± 2.3 |
| Trial 6 | 10 h | 1000° C. | 24.4 ± 1.1 |

*) Information in % by weight, residue Co and unavoidable impurities

TABLE 7

| VARIANT VII | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | 3.0-9.0 | — | — | 0.1-6.0 | — | <1.0 | <3.0 | <3.0 |
| Optimal *) | <0.1 | 0.8-2.0 | 23-27 | 4.0-6.0 | — | — | 2.0-4.0 | — | <0.5 | <0.1 | <0.5 |
| Soft variant *) | <0.1 | 0.8-2.0 | 23-27 | 4.0-6.0 | — | — | 0.1-3.0 | — | <0.5 | <0.1 | <0.5 |
| Hard variant *) | <0.1 | 0.8-2.0 | 23-27 | 4.0-6.0 | — | — | 3.0-6.0 | — | <0.5 | <0.1 | <0.5 |
| Examined example *) | 0.019 | 1.23 | 25.06 | 4.76 | — | — | 3.62 | — | <0.01 | <0.01 | 0.11 |

| Solution-annealing | Duration | Temperature | Hardness in HRC after solution-annealing |
|---|---|---|---|
| | 8 | 1250 | 20.4 ± 1.5 |

| Ageing | Duration | Temperature | Hardness in HRC after ageing |
|---|---|---|---|
| Trial 1 | 10 h | 500° C. | 17.3 ± 2.3 |
| Trial 2 | 10 h | 600° C. | 17.5 ± 2.7 |
| Trial 3 | 10 h | 700° C. | 20.3 ± 1.4 |
| Trial 4 | 10 h | 800° C. | 41.8 ± 2.6 |
| Trial 5 | 10 h | 900° C. | 43.4 ± 1.7 |
| Trial 6 | 10 h | 1000° C. | 35.7 ± 1.1 |

*) Information in % by weight, residue Co and unavoidable impurities

TABLE 8

| VARIANT VIII | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | 3.0-9.0 | — | 0.1-6.0 | — | <1.0 | <3.0 | <3.0 |
| Optimal *) | <0.1 | 0.8-2.0 | 23-27 | — | 4.0-6.0 | — | 2.0-4.0 | — | <0.5 | <0.1 | <0.5 |
| Soft variant *) | <0.1 | 0.8-2.0 | 23-27 | — | 4.0-6.0 | — | 0.1-3.0 | — | <0.5 | <0.1 | <0.5 |

TABLE 8-continued

| | | | | | | | | | | | |
|---|---|---|---|---|---|---|---|---|---|---|---|
| Hard variant *) | <0.1 | 0.8-2.0 | 23-27 | — | 4.0-6.0 | — | 3.0-6.0 | — | <0.5 | <0.1 | <0.5 |
| Examined example *) | 0.036 | 1.26 | 25.29 | — | 4.92 | — | 3.4 | — | <0.01 | 0.03 | 0.07 |

| Solution-annealing | Duration | Temperature | Hardness in HRC after solution-annealing |
|---|---|---|---|
| | 8 | 1250 | 21.6 ± 1.2 |

| Ageing | Duration | Temperature | Hardness in HRC after ageing |
|---|---|---|---|
| Trial 1 | 10 h | 500° C. | 18.7 ± 1.4 |
| Trial 2 | 10 h | 600° C. | 17.3 ± 1.2 |
| Trial 3 | 10 h | 700° C. | 18.4 ± 2.1 |
| Trial 4 | 10 h | 800° C. | 29.6 ± 2.1 |
| Trial 5 | 10 h | 900° C. | 36.1 ± 1.3 |
| Trial 6 | 10 h | 1000° C. | 31.4 ± 1.5 |

*) Information in % by weight, residue Co and unavoidable impurities

TABLE 9

| VARIANT IX | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | — | — | 3.0-9.0 | 0.1-6.0 | — | <1.0 | <3.0 | <3.0 |
| Optimal *) | <0.1 | 0.8-2.0 | 23-27 | — | — | 4.0-6.0 | 2.0-4.0 | — | <0.5 | <0.1 | <0.5 |
| Soft variant *) | <0.1 | 0.8-2.0 | 23-27 | — | — | 4.0-6.0 | 0.1-3.0 | — | <0.5 | <0.1 | <0.5 |
| Hard variant *) | <0.1 | 0.8-2.0 | 23-27 | — | — | 4.0-6.0 | 3.0-6.0 | — | <0.5 | <0.1 | <0.5 |
| Examined example *) | 0.019 | 1.40 | 25.39 | — | — | 5.73 | 3.50 | — | <0.01 | 0.04 | 0.08 |

| Solution-annealing | Duration | Temperature | Hardness in HRC after solution-annealing |
|---|---|---|---|
| | 8 | 1250 | 27.0 ± 1.5 |

| Ageing | Duration | Temperature | Hardness in HRC after ageing |
|---|---|---|---|
| Trial 1 | 10 h | 500° C. | 26.6 ± 2.6 |
| Trial 2 | 10 h | 600° C. | 29.3 ± 3.1 |
| Trial 3 | 10 h | 700° C. | 29.0 ± 2.8 |
| Trial 4 | 10 h | 800° C. | 46.1 ± 1.8 |
| Trial 5 | 10 h | 900° C. | 43.5 ± 1.6 |
| Trial 6 | 10 h | 1000° C. | 39.3 ± 1.8 |

*) Information in % by weight, residue Co and unavoidable impurities

TABLE 10

| VARIANT X | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | 3.0-9.0 | 3.0-9.0 | — | 0.1-6.0 | — | <1.0 | <3.0 | <3.0 |
| Optimal *) | <0.1 | 0.8-2.0 | 23-27 | 4.0-6.0 | 4.0-6.0 | — | 2.0-4.0 | — | <0.5 | <0.1 | <0.5 |
| Soft variant *) | <0.1 | 0.8-2.0 | 23-27 | 4.0-6.0 | 4.0-6.0 | — | 0.1-3.0 | — | <0.5 | <0.1 | <0.5 |
| Hard variant *) | <0.1 | 0.8-2.0 | 23-27 | 4.0-6.0 | 4.0-6.0 | — | 3.0-6.0 | — | <0.5 | <0.1 | <0.5 |
| Examined example *) | 0.045 | 1.35 | 25.02 | 4.85 | 4.83 | — | 3.46 | — | <0.01 | 0.05 | 0.07 |

| Solution-annealing | Duration | Temperature | Hardness in HRC after solution-annealing |
|---|---|---|---|
| | 8 | 1250 | 34.0 ± 1.2 |

| Ageing | Duration | Temperature | Hardness in HRC after ageing |
|---|---|---|---|
| Trial 1 | 10 h | 500° C. | 30.7 ± 2.7 |
| Trial 2 | 10 h | 600° C. | 33.0 ± 1.4 |
| Trial 3 | 10 h | 700° C. | 34.9 ± 1.5 |
| Trial 4 | 10 h | 800° C. | 53.7 ± 1.3 |
| Trial 5 | 10 h | 900° C. | 51.7 ± 2.1 |
| Trial 6 | 10 h | 1000° C. | 47.1 ± 1.7 |

*) Information in % by weight, residue Co and unavoidable impurities

TABLE 11

| VARIANT XI | C | Si | Cr | Mo | W | Nb | Al | Ti | Mn | Ni | Fe |
|---|---|---|---|---|---|---|---|---|---|---|---|
| General *) | <0.5 | ≤2.5 | 22-29 | 3.0-9.0 | — | — | — | 0.1-5.0 | <0.1 | <3.0 | <3.0 |
| Optimal *) | <1.0 | 0.8-2.0 | 23-27 | 4.0-6.0 | — | — | — | 1.0-3.0 | <0.5 | <0.1 | <0.5 |
| Soft variant *) | <0.1 | 0.8-2.0 | 23-27 | 4.0-6.0 | — | — | — | 0.1-2.0 | <0.5 | <0.1 | <0.5 |

TABLE 11-continued

| Hard variant *) | <0.1 | 0.8-2.0 | 23-27 | 4.0-6.0 | — | — | — | 2.0-5.0 | <0.5 | <0.1 | <0.5 |
| Examined example *) | 0.005 | 1.97 | 25.02 | 5.07 | — | — | — | 1.86 | <0.01 | 0.03 | 0.08 |

| Solution-annealing | Duration | Temperature | Hardness in HRC after solution-annealing |
| --- | --- | --- | --- |
|  | 8 | 1250 | 25.2 ± 0.4 |

| Ageing | Duration | Temperature | Hardness in HRC after ageing |
| --- | --- | --- | --- |
| Trial 1 | 10 h | 500° C. | 22.0 ± 1.9 |
| Trial 2 | 10 h | 600° C. | 27.0 ± 1.8 |
| Trial 3 | 10 h | 700° C. | 30.9 ± 1.8 |
| Trial 4 | 10 h | 800° C. | 48.0 ± 2.5 |
| Trial 5 | 10 h | 900° C. | 44.2 ± 2.0 |
| Trial 6 | 10 h | 1000° C. | 40.8 ± 2.9 |

*) Information in % by weight, residue Co and unavoidable impurities

TABLE 12

| Variant: | VII | VIII | IX | X | XI |
| --- | --- | --- | --- | --- | --- |
| Hardness in HRC after solution-annealing: | 20.4 ± 1.5 | 21.6 ± 1.2 | 27.0 ± 1.5 | 34.0 ± 1.2 | 25.2 ± 0.4 |

| Ageing Temperature/ Duration | Hardness in HRC after ageing: | | | | |
| --- | --- | --- | --- | --- | --- |
| 800° C./20 min | 20.2 ± 1.2 | 18.3 ± 0.5 | 27.5 ± 2.9 | 32.8 ± 1.3 | 21.3 ± 1.4 |
| 800° C./40 min | 21.0 ± 1.9 | 19.0 ± 2.0 | 30.6 ± 4.0 | 33.2 ± 0.8 | 23.8 ± 1.8 |
| 800° C./60 min | 21.0 ± 2.2 | 17.8 ± 1.0 | 32.8 ± 2.5 | 35.3 ± 2.1 | 24.0 ± 2.4 |
| 800° C./80 min | 31.7 ± 3.4 | 23.4 ± 2.3 | 40.8 ± 2.8 | 50.3 ± 2.2 | 35.0 ± 1.6 |
| 800° C./100 min | 41.3 ± 1.5 | 29.3 ± 2.2 | 43.7 ± 0.8 | 50.3 ± 2.2 | 35.0 ± 1.6 |
| 800° C./120 min | 42.8 ± 1.9 | 29.0 ± 1.7 | 46.0 ± 1.1 | 52.8 ± 2.0 | 36.4 ± 1.5 |
| 800° C./10 h | 41.8 ± 2.6 | 29.6 ± 2.1 | 46.1 ± 1.8 | 53.7 ± 1.3 | 48.0 ± 2.5 |

The invention claimed is:

1. A method for producing an implant or a prosthesis, comprising:
   providing a soft blank, comprising a precipitation-hardening or solid-solution-strengthening, biocompatible cobalt-based alloy;
   carving an implant or a prosthesis out of the soft blank using material-removing machining; and
   heat-treating the implant or the prosthesis to adjust a final hardness by precipitation hardening or solid-solution strengthening,
   wherein the cobalt-based alloy comprises (in % by weight),
   C: up to 0.1%,
   Si: 0.8-2.0%,
   Cr: 22-29%,
   Mn: up to 1%,
   Ni: up to 3%,
   Fe: up to 3%,
   Ce: up to 1%,
   Ga: up to 5%, and
   B: up to 2.5%,
   and at least one hardening precipitation or solid-solution-forming element is selected from the group consisting of Mo, W, Nb, Al, and Ti, wherein for the concentrations of these elements, where present, the following proportions apply,
   Mo: 3-9%,
   W: 3-9%,
   Nb: 3-9%,
   Al: 0.1-6%, and
   Ti: 0.1-6%,
   and wherein the remainder is Co and unavoidable impurities resulting from production.

2. The method according to claim 1, wherein the blank is a disc from which each implant or each prosthesis is carved by milling.

3. The method according to claim 1, wherein the Cr concentration of the cobalt-based alloy is 23-27% by weight.

4. The method according to claim 1, wherein, for the concentrations of the hardening precipitation or solid-solution-forming elements present in the cobalt-based alloy, the following proportions apply (in % by weight):
   Mo: 4-6%,
   W: 4-6%,
   Nb: 4-6%,
   Al: 2-4%, and
   Ti: 1-3%.

5. The method according to claim 1, wherein (in % by weight) the Mn concentration of the cobalt-based alloy is at most 0.5%, or the Ni concentration of the cobalt-based alloy is at most 0.1%.

6. The method according to claim 1, wherein in each case at least two elements forming hardening precipitates are present in the cobalt-based alloy.

7. The method according to claim 1, wherein the blank is solution-annealed before the material-removing machining thereof at a temperature of from 1050-1300° C. over a period of from 15-600 min.

8. The method according to claim 7, wherein, after the solution-annealing, the blank is cooled to room temperature at a cooling speed of from 5-1000 K/min.

9. The method according to claim 1, wherein the implant or prosthesis is heat treated at an ageing temperature of from 600-1000° C. for an ageing period of at least 5 min and at most 600 min in order to adjust the hardness thereof.

10. The method according to claim 9, wherein the ageing temperature is at least 700° C.

11. The method according to claim 9, wherein the ageing period is from 5-150 min.

* * * * *